(12) United States Patent
Olesen et al.

(10) Patent No.: US 10,912,461 B2
(45) Date of Patent: Feb. 9, 2021

(54) METHOD FOR SURFACE SCANNING IN MEDICAL IMAGING AND RELATED APPARATUS

(71) Applicant: DANMARKS TEKNISKE UNIVERSITET, Kgs. Lyngby (DK)

(72) Inventors: Oline Olesen, Søborg (DK); Rasmus Larsen, Gentofte (DK); Jakob Wilm, Copenhagen (DK); Rasmus Ramsbøl Jensen, Frederiksberg (DK)

(73) Assignee: DANMARKS TEKNISKE UNIVERSITET, Kgs. Lyngby (DK)

( * ) Notice: Subject to any disclaimer, the term of this patent is extended or adjusted under 35 U.S.C. 154(b) by 92 days.

(21) Appl. No.: 15/035,507

(22) PCT Filed: Nov. 13, 2014

(86) PCT No.: PCT/EP2014/074509
§ 371 (c)(1),
(2) Date: May 10, 2016

(87) PCT Pub. No.: WO2015/071369
PCT Pub. Date: May 21, 2015

(65) Prior Publication Data
US 2016/0287080 A1    Oct. 6, 2016

(30) Foreign Application Priority Data

Nov. 13, 2013    (EP) .................................... 13192786

(51) Int. Cl.
*A61B 5/00*    (2006.01)
*A61B 6/00*    (2006.01)
(Continued)

(52) U.S. Cl.
CPC .......... *A61B 5/0064* (2013.01); *A61B 5/0046* (2013.01); *A61B 5/055* (2013.01);
(Continued)

(58) Field of Classification Search
None
See application file for complete search history.

(56) References Cited

U.S. PATENT DOCUMENTS

| 4,796,969 A | 1/1989 | Fantone |
| 5,802,224 A * | 9/1998 | Okuta ...................... G02B 6/34 385/43 |

(Continued)

FOREIGN PATENT DOCUMENTS

EP    1513446    3/2005

OTHER PUBLICATIONS

Olesen et al. ("structured light 3D tracking system for measuring motions in PET brain imaging", Proc. of SPIE vol. 7625 762250X-1, 2010).*

(Continued)

*Primary Examiner* — Oommen Jacob
*Assistant Examiner* — Shahdeep Mohammed
(74) *Attorney, Agent, or Firm* — Duane Morris LLP; Gregory M. Lefkowitz; Jason M. Nolan

(57) ABSTRACT

A method and apparatus for surface scanning in medical imaging is provided. The surface scanning apparatus comprises an image source, a first optical fiber bundle comprising first optical fibers having proximal ends and distal ends, and a first optical coupler for coupling an image from the image source into the proximal ends of the first optical fibers, wherein the first optical coupler comprises a plurality of lens elements including a first lens element and a second lens element, each of the plurality of lens elements comprising a primary surface facing a distal end of the first optical coupler, and a secondary surface facing a proximal end of the first optical coupler.

23 Claims, 5 Drawing Sheets

(51) Int. Cl.
*A61B 5/055* (2006.01)
*A61B 5/11* (2006.01)
*A61B 6/03* (2006.01)
*G02B 6/32* (2006.01)

(52) U.S. Cl.
CPC ............ *A61B 5/1128* (2013.01); *A61B 5/721* (2013.01); *A61B 6/032* (2013.01); *A61B 6/037* (2013.01); *A61B 6/527* (2013.01); *A61B 2562/228* (2013.01); *G02B 6/32* (2013.01)

(56) References Cited

U.S. PATENT DOCUMENTS

| 6,768,593 | B1 | 7/2004 | Jutamulia | |
|---|---|---|---|---|
| 2004/0111032 | A1 | 6/2004 | Korn | |
| 2009/0039235 | A1* | 2/2009 | MacFarlane | G01R 33/28 250/206.1 |
| 2012/0123205 | A1 | 5/2012 | Nie et al. | |
| 2012/0203075 | A1* | 8/2012 | Horvath | A61B 1/07 600/249 |
| 2013/0002832 | A1 | 1/2013 | Lasenby et al. | |
| 2013/0093866 | A1 | 4/2013 | Ohlhues et al. | |
| 2013/0342838 | A1* | 12/2013 | Kinugasa | G01N 15/1434 356/338 |
| 2014/0187968 | A1* | 7/2014 | Pinho | A61B 5/0059 600/476 |
| 2015/0359464 | A1 | 12/2015 | Olesen et al. | |

OTHER PUBLICATIONS

Oline Vinter Olesen et al: "Motion Tracking for Medical Imaging: A Nonvisible Structured Light Tracking Approach", IEEE Transactions on Medical Imaging, IEEE Service Center, Piscataway, NJ, US, vol. 31, No. 1, Jan. 1, 2012 (Jan. 1, 2012), pp. 79-87, XP011391090, ISSN: 0278-0062, DOI: 10.1109/TMI.2011.2165157.

Jason Geng: "Structured-light 3D surface imaging: a tutorial", Advances in Optics and Photonics, vol. 3, No. 2, Mar. 31, 2011 (Mar. 31, 2011), p. 128, XP055033088, DOI: 10.1364/AOP.3.000128.

* cited by examiner

METHOD FOR SURFACE SCANNING IN MEDICAL IMAGING AND RELATED APPARATUS

CROSS-REFERENCE TO RELATED APPLICATIONS

This application is a § 371 national stage entry of International Application No. PCT/EP2014/074509, filed Nov. 13, 2014, which claims priority to European Patent Application No. 13192786.5 filed Nov. 13, 2013, the entire contents of which is incorporated herein by reference.

The present invention relates to a method and apparatus for surface scanning in medical imaging, in particular in magnetic resonance imaging (MRI), in positron emission tomography (PET), and/or in combined MRI/PET. The invention may be used for surface scanning/motion tracking in particular inside small geometries (in-bore of PET, MRI, CT, SPECT or combined scanners as PET/CT and MRI/PET).

BACKGROUND

Over the last decade, numerous methods for surface scanning and motion tracking in brain imaging have been developed, but head motion during scanning pertains to be a significant problem causing artefacts and significantly reducing image quality.

Known methods include external tracking systems as well as image based motion tracking and correction. Many external tracking systems use markers attached to the subjects head. This potentially introduces errors and complicates the process of preparing the subject for the scan and therefore reduces the usability in clinical practice. Correspondingly, the image based motion tracking methods developed for medical brain imaging generally suffer from an inability to obtain sufficiently high temporal and spatial resolution at the same time. Further, the high resolution of modern medical scanners (down to tenths of a millimeter for MRI and a few millimeters for PET) set strict requirements to motion tracking systems.

SUMMARY

The present invention relates to a method and apparatus for improved surface scanning in medical imaging. Disclosed herein is therefore a method for surface scanning in medical imaging that may be used for subject tracking, the method comprising a) providing an image source and a first fiber bundle comprising first optical fibers having proximal ends and distal ends; b) positioning the distal ends of the first optical fibers within a scanner borehole of a medical scanner; c) feeding an image from the image source into a proximal end of a first optical coupler, the first optical coupler comprising a plurality of lens elements including a first lens element and a second lens element; and d) feeding an image from a distal end of the first optical coupler into the proximal ends of the first optical fibers.

Disclosed herein is also a surface scanning apparatus for surface scanning in medical imaging, the apparatus comprising a) an image source, b) a first optical fiber bundle comprising first optical fibers having proximal ends and distal ends, and c) a first optical coupler for coupling an image from the image source into the proximal ends of the first optical fibers, wherein the first optical coupler comprises a plurality of lens elements including a first lens element and a second lens element, each of the plurality of lens elements comprising a primary surface facing a distal end of the first optical coupler, and a secondary surface facing a proximal end of the first optical coupler.

By the above method and/or surface scanning apparatus is obtained an improved surface scanning method and/or motion tracking method wherein components that generate noise, such as radio emitting components and/or ferromagnetic components, are separated form and kept out of the bore. Further, occlusion effects are highly reduced if not completely avoided. Further, an improved image quality on the object which is scanned in the borehole is provided. Problems previously observed regarding a decrease in image quality due to long distances between scanner and light source is avoided due to the use of optical fibers, which ensures a high image quality even over larger distances.

The method may be particularly useful in a method for motion tracking in medical imaging, and the surface scanning apparatus may be a motion tracking apparatus By the method and/or surface scanning apparatus is further obtained a very compact device, which can easily be incorporated into a scanner or be used as an add-on to existing scanning systems.

BRIEF DESCRIPTION OF THE DRAWINGS

The above and other features and advantages of the present invention will become readily apparent to those skilled in the art by the following detailed description of exemplary embodiments thereof with reference to the attached drawings, in which.

DETAILED DESCRIPTION

Figure 1A:
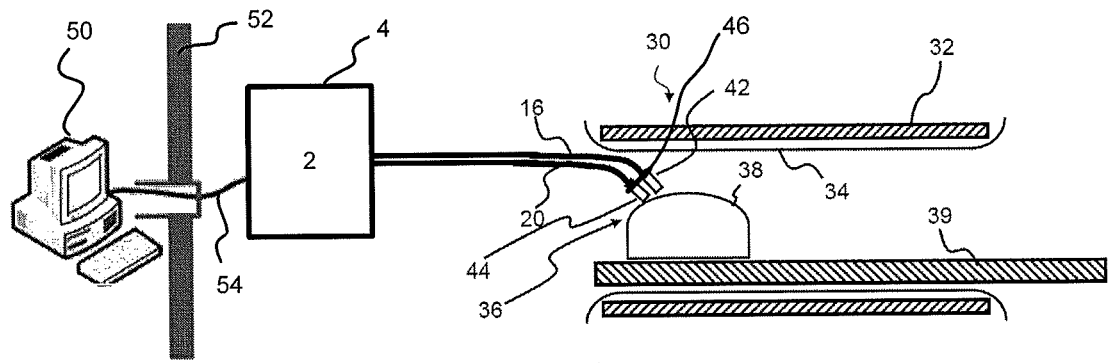
FIG. 1a schematically illustrates a surface scanning apparatus in connection with a medical scanner and a computer system, FIG. 1b schematically illustrates an exemplary surface scanning apparatus, FIG. 2 schematically illustrates parts of an exemplary surface scanning apparatus, FIG. 3 schematically illustrates parts of an exemplary surface scanning apparatus, FIG. 4 schematically illustrates parts of an exemplary surface scanning apparatus, FIG. 5 schematically illustrates parts of an exemplary surface scanning apparatus, FIG. 6a schematically illustrates decreasing of the image size with different lens elements in an optical coupler, FIG. 6b schematically illustrates increasing of the image size with different lens elements in an optical coupler, FIG. 7a schematically illustrates a relay lens coupler, and FIG. 7b schematically illustrates an alternative relay lens coupler.

The figures are schematic and simplified for clarity, and they merely show details which are essential to the understanding of the invention, while other details may have been left out. Throughout, the same reference numerals are used for identical or corresponding parts.

Surface scanning incorporates tracking spatial position of a surface or surface points over time and/or tracking/determining spatial position of a surface or surface points at a given time.

The medical scanner may be a magnetic resonance (MR) scanner. Further, the method and apparatus for motion tracking may be employed for motion correction of scanning images obtained by other medical scanners, such as a positron emission tomography (PET) scanner, a single photon emission computed tomography (SPECT) scanner or a computed tomography (CT) scanner. In one or more aspects, the method and apparatus may be employed for motion correction of a subject in a combined PET-MR scanner or a combined PET-CT scanner.

The image source provided in the method or the apparatus may include a light source and/or a digital micromirror device (DMD) chip, where the DMD chip is for modulating the incoming light from the light source thus creating a pre-determined image source.

The image source may be a modified DLP (digital light processing) projector.

Feeding an image, e.g. from the image source into a proximal end of a first optical coupler and/or from a distal end of the first optical coupler into the proximal ends of the first optical fibers, may comprise feeding a pattern sequence comprising a pattern or a plurality of different patterns.

The image source may be configured for providing a pattern sequence, e.g. comprising a plurality of different patterns, e.g. for projection of patterns onto the surface region or scene of the subject in the borehole. A pattern sequence (S), e.g. a first pattern sequence (S1) and/or a second pattern sequence (S2), comprises one or more patterns (P), such as a plurality of different patterns including a primary pattern and a secondary pattern. A pattern sequence comprises or consists of a number N of patterns. A pattern sequence may be defined by pattern sequence parameters, for example including number of patterns, configuration/structure of respective patterns, order of patterns and/or timing of pattern(s) of the pattern sequence. The duration of a pattern sequence may be in the range from 1 millisecond to about 1 second. The duration of a pattern sequence may be about 10 milliseconds, about 20 milliseconds, about 50 milliseconds, about 100 milliseconds or about 200 milliseconds.

A pattern may comprise a number of pixels, e.g. arranged in an array along a first and second axis. A pattern may be defined by pattern parameters, e.g. including pixel settings (color/wavelength and/or intensity) of each pixel and/or one or more groups of pixels in the pattern. A group of pixels of a pattern may be referred to as a subregion denoted R of a pattern. Accordingly, a pattern may comprise one or more subregions $R_1$, $R_2$, $R_3$, . . . , a subregion comprising one or more pixels. Pattern sequence parameters may include pattern parameters, e.g. of a primary pattern, a secondary pattern and/or a tertiary pattern.

The image source may comprise a light modulator.

The light modulator or DMD chip can be adapted for projection of patterns onto the surface region or scene of the subject in the borehole. The light modulator may comprise a liquid crystal display (LCD) chip or a DMD chip. In one or more embodiments, the light modulator may comprise a liquid crystal on silicon (LCOS) chip. In one or more embodiments, the light modulator may comprise grids, slits or filters. The light modulator may be a transmitting or reflective light modulator.

The DMD chip/light modulator may be an array which is approximately 9.86 mm times 6.16 mm and images from the DMD chip/light modulator are mapped with the first optical coupler into a first fiber bundle with proximal end size of about 6.7 mm times 5 mm.

The image source may be connected to a control unit for receiving control signal(s) from the control unit. The control signal(s) may comprise pattern sequence parameters, such as number, configuration, order and/or timing of pattern(s) of the pattern sequence. In one or more embodiments, the control signal(s) may comprise a pattern sequence selector, and the image source may be configured for projecting different pattern sequences dependent on the pattern sequence selector.

The resolution of the image source and/or first fiber bundle limits the pattern resolution projected onto the subject. The image source may have a resolution of at least 500 pixels, such as at least 1,000 pixels or at least 10,000 pixels in order to project a useful image on the subject. In an exemplary method and/or apparatus, the image source may have a resolution of HVGA (480×320 pixels) or more, e.g. (608×684 pixels), SVGA (800×600 pixels), XGA (1024× 768 pixels), 720p (1280×720 pixels), or 1080p (1920×1080 pixels).

In one or more embodiments, a number of different pattern sequences may be stored in the image source, and the image source may be configured to project a selected pattern sequence based on a pattern sequence selector from a control unit.

In an embodiment, the light source may include one or more lasers or (high power) LED's including a first laser/ LED configured to emit light at the first wavelength $\lambda_1$ and/or a second laser/LED configured to emit light at a second wavelength $\lambda_2$. The light source may also include a third laser/LED configured to emit light at a third wavelength $\lambda_3$.

The light source may include a broad spectrum light source, such as a metal-halide lamp. In one or more embodiments, the light source may comprise a light emitting diode (LED). The light source may comprise a filter for forming light with desired frequency spectrum/wavelength distribution. In one or more embodiments, the light source may be adapted to emit light in the infrared (IR) or near-infrared (NIR) range, for example at a wavelength in the range from 700 nm to about 1,000 nm, e.g. about 850 nm. In one or more embodiments, the light source may be adapted to emit light in the UV range.

In one or more embodiments, the image source may comprise light at a first wavelength $\lambda_1$ in the range from 780-900 nm. For example, the wavelength range may be between 800-860 nm. The first laser/LED may be a red or orange/red laser, wherein the first wavelength $\lambda_1$ is in the range from about 590 nm to about 700 nm. In one or more embodiments the first wavelength $\lambda_1$ is about 635 nm. The first laser/LED may be an LED, wherein the first wavelength $\lambda_1$ is in the range from about 830 nm to about 870 nm, e.g. about 850 nm or from about 810 nm to about 850 nm. The first laser/LED may be an LED, wherein the first wavelength $\lambda_1$ is in the range from about 790 nm to about 830 nm, e.g. about 810 nm or from about 800 nm to about 820 nm.

The second laser/LED may be a green laser, wherein the second wavelength $\lambda_2$ is in the range from about 490 nm to about 560 nm, e.g. about 532 nm. The second laser/LED may be an LED, wherein the second wavelength $\lambda_2$ is in the range from about 880 nm to about 920, e.g. about 900 nm.

The third laser/LED may be a blue or violet laser, e.g. wherein the third wavelength $\lambda_3$ is in the range from 430 nm to about 490 nm, e.g. about 445 nm or about 473 nm. The third laser/LED may be an LED, e.g. wherein the third wavelength $\lambda_3$ is in the range from 930 nm to about 1,000 nm, e.g. about 940 nm.

The light source may comprise a UV source, e.g. configured to emit light with a wavelength in the range from about 230 nm to about 400 nm, e.g. about 350 nm.

One or more mirrors or a prism may be used to guide light or an image from the light source and/or image source to the first optical coupler. Different examples of this are shown and described in connection with FIG. 2-5.

The first optical coupler may comprise or consist of an even number of lens elements, e.g. two, four, six, eight, ten, twelve or more lens elements. In one or more embodiments, ten lenses are included in the first optical coupler. In another embodiment, six lenses are included in the first optical coupler. When choosing a lower number of lenses, the optical loss is kept at a minimum, whereas when choosing a many lenses, the image quality is improved and the distortion and blurriness are reduced. The relay lens element may comprise between four and twelve lens elements.

The first optical coupler may be adapted for either increasing or decreasing the size of the image after the image has passed through the first optical coupler. In an exemplary method/apparatus, the lens elements in the first optical coupler maps the incoming image size by a ratio of 1:1.2, thus the image size of the image coming out of the distal end of the first optical coupler is 20% larger compared to the size of the image entering the first optical coupler at its proximal end. In general, the image size can be mapped in the range from 1:0.5 (i.e. the out-coming image is 50% smaller than the incoming image) to 1:2.

Advantageously, the first optical coupler may be a relay lens coupler.

The distal end of the first optical coupler may be secured releasably to the proximal end of the first fiber bundle by a click-release-coupling. This allows for an easy and flexible positioning of the optical fibers in the borehole of the scanner or an easy replacement and/or exchange of the optical fibers or the first optical coupler without moving the other of the two.

Alternatively, for ensuring a constant optimum coupling of the image from the first optical coupler into the optical fibers, the distal end of the first optical coupler may be fixed non-releasably to the proximal end of the first fiber bundle.

A second optical coupler comprising a plurality of lens elements including a first lens element and a second lens element may also be included in the surface scanning apparatus and/or the method for tracking the motion. Also, a second fiber bundle comprising second optical fibers having proximal ends and distal ends can be provided and its distal ends positioned within the scanner borehole of the medical scanner. The distal ends of the second optical fibers may be applied for capturing a projected image from a subject in the borehole. This projected image will normally be fed from the proximal ends of the second optical fibers into the second optical coupler.

The second optical coupler may also be adapted for either increasing or decreasing the size of the projected image after the image has passed through the second optical coupler.

At least one of the plurality of lens elements in the first and/or second optical coupler may be achromatic.

In an embodiment of the invention, the first lens element in the first and/or second optical coupler can be positioned at the proximal end of the first and/or second optical coupler, respectively, and the second lens element can be positioned at the distal end of the first and/or second optical coupler, respectively. The first lens element and the second element may further be achromatic with convex sides pointing towards each other.

The primary surface of each of the plurality of lens elements in the first and/or second optical coupler may be concave or convex or planar or a combination thereof. Likewise, the secondary surface of each of the plurality of lens elements in the first and/or second optical coupler may be concave or convex or planar or a combination thereof. The primary surface of one or more lens elements may be concave. The primary surface of one or more lens elements may be convex. The primary surface of one or more lens elements may be plane. The secondary surface of one or more lens elements may be concave. The secondary surface of one or more lens elements may be convex. The secondary surface of one or more lens elements may be plane.

The apparatus and the method may further comprise a mirror and/or a prism, and light from the light source may pass the mirror/prism before entering the first optical coupler.

The first optical fibers may further be adapted for projecting at least one pattern from the image source via the first optical fibers onto the surface region of the subject positioned in a borehole of the medical scanner.

The first optical fibers may comprise at least 100 optical fibers, such as at least 10,000 fibers, each fiber corresponding to a pixel in a pattern projected onto the surface region of the subject. In one or more embodiments, the number of first optical fibers is equal to or larger than the number of pixels in the image source, for full benefit of the image source resolution. The number of first optical fibers may match or be in the range of ±20% of the resolution of the image source. In one or more embodiments, the number of first optical fibers is less than the number of pixels in the image source, for full benefit of the optical fibers.

The second optical fibers can be adapted for capturing at least one projected pattern and/or image projected form the subject. The second optical fibers may comprise at least 100 optical fibers, such as at least 100,000 fibers. Each second optical fiber may correspond to one or more pixels in a first camera, which the captured image is transmitted to. In one or more embodiments, the number of second optical fibers is equal to or larger than the number of pixels in the first camera for increasing the processing time of the camera. In one or more embodiments, the number of second optical fibers is less than the number of pixels in the first camera for increasing the precision of the image capturing. The number of second optical fibers may match or be in the range of ±50% of the resolution of the first camera.

The first camera may be a CCD camera or a CMOS camera. The first camera may have a resolution of at least 640×480, e.g. 1280×960, 3264×2448 or more.

The surface region may have an area of at least $0.1$ $cm^2$, e.g. in the range from 1 $cm^2$ to 500 $cm^2$. In one or more embodiments, the surface region area may be in the range from 20 $cm^2$ to 100 $cm^2$.

The surface region may at least partly cover a nasal region of the subject. This may lead to improved motion tracking due to the significant curvature of the subject surface in this region. Further, facial movements are limited near the bridge of the nose which is preferred when tracking the motion of the scull and the brain.

The apparatus may also comprise a first lens assembly, i.e. projector side projection optics, arranged at and/or attached to the distal end of the first optical fibers for coupling images or pattern sequences from the first optical fibers to the surface region of the subject. The distal ends of the second optical fibers may be provided with a second lens assembly, i.e. image capturing optics, for coupling images or pattern sequences from the surface region of the subject to the second optical fibers.

The apparatus may comprise a frame, wherein the first and second lens assemblies are mounted on the frame. The frame fixes the position between the two distal ends of the fibers bundles and/or between the first and second lens assemblies to maintain a fixed positional relationship in order to provide an accurate movement correction and/or such that the two fiber bundles can be moved together inside the borehole. The distal ends of the first and the second fiber bundles may be mounted on the frame.

The first and second lens assemblies will normally comprise an objective lens with a given focal length and an aperture. The focal length may be changed by exchanging the objective lens. Also by changing the distance between the objective lens and the distal ends of the optical fibers in the first or second optical fiber bundle, control of how much of the image source illuminates the subject and which area projected light is captured from, respectively, can be obtained. The aperture in the first and/or second lens assemblies may be adjusted by opening and/or closing them, which also provides a tool for controlling the output from the first optical fibers onto the subject, and the projected image from the subject into the second optical fibers for the first lens assembly and the second lens assembly, respectively.

The second lens assembly may also comprise a filter, e.g. a NIR filter. Likewise, the first lens assembly may also comprise a filter.

The first lens assembly may comprise a first mirror/prism. The second lens assembly may comprise a second mirror/prism, respectively. A common mirror/prism may be shared between the first lens assembly and the second lens assembly. A mirror/prism in a lens assembly may provide redirection of the light which may lead to larger freedom in positioning the distal fiber ends/lens assemblies in the bore.

The first and second optical fibers may be arranged in respective first and second fiber arrays. In one or more embodiments, the first optical fibers may comprise a first array of at least 10,000 fibers, such as 100×100 fibers, such as 400×400 or 600×600 fibers or 680×480 fibers or 1,200×1,200 fibers or more. The first optical fibers may comprise a first array of at least 100,000 fibers, e.g. 5,000×5,000 fibers. In one or more embodiments, the second optical fibers comprise a second array of at least 10,000 fibers, such as 100×100 fibers, such as at least 400×400 or 600×600 fibers or 680×480 fibers or 1,200×1,200 fibers, or more. The second optical fibers may comprise a second array of at least 100,000 fibers, e.g. 5,000×5,000 fibers. The optical fibers may be arranged in an array of any suitable size and shape, e.g. rectangular, circular, oval, polygonal or others. Typically, the fiber diameter is in the range from 5 to 20 micrometers. The number of first optical fibers may be larger than 1,000, such as larger than 10,000. The number of second optical fibers may be larger than 1,000, such as larger than 10,000.

Using first and second optical fibers enables or facilitates the use of the method and apparatus for medical scanners with a permanent magnetic field surrounding the object, e.g. an MR scanner. Further, using first and second optical fibers enables or facilitates the use of the method and apparatus for medical scanners with limited access to the subject due to the subject being positioned in a scanner borehole during scanning.

The first and second fiber bundles may each have a length larger than 1 meter, such as larger than 2 meters, e.g. about 5 meters or about 10 meters. In an exemplary apparatus and/or method, the first and second fiber bundles may each have a length between 1 and 5 meters, such as between 2.5 and 3 meters, for example about 2.7 meters. Having a length of the fiber bundles in this length range may enable the user to place the distal ends of the first and second fiber bundles inside the scanner while keeping the first and/or second optical couplers at a different location remote from the scanner or even remote from/outside the scanning room.

The length of the fiber bundles allows for positioning of a power management part and/or a computer for controlling a sequence, an image pattern or similar relating to the image source, outside the room with the scanner. This allows for the creation of a remote surface scanner. By separating the electronics from the optical end by the two fibers bundles, a compact, radio frequency noiseless and low attenuation surface scanner is achieved.

In the apparatus and method of this invention, a minimum of components are located in the borehole of the scanner and the disturbing components are kept outside the borehole. This maintains the field of view and the high resolution of nowadays surface scanners. Further, the components located in the borehole of the scanner may be made of non-metallic materials.

The surface scanning apparatus may also comprise a housing which surrounds all the motion tracking elements apart from the fibers bundles which extend from the surface of the housing. The housing may be a radio frequency shielded box costume normally made out of a frame covered by a thin copper layer or sheet, e.g. of a thickness of 1 mm. Any metal suited for shielding the electric components may be used.

A filter of one or more capacitors may ensure that the electromagnetic noise from powering the components inside the housing does not propagate along the power cable. Correspondingly, a power supply is positioned outside the scanner room and the power is led though a filter in the wall into the scanner room and the inside of the housing to feed the relevant components therein.

The surface scanning apparatus may be constructed such that it is part of the medical scanner or be used as an add-on to existing scanners.

FIG. 1a schematically illustrates a medical scanner 30 for use with the method and apparatus. The scanner 30 is an MR scanner comprising a permanent magnet 32 in a scanner housing 34 forming a scanner borehole 36. The scanner 30 comprises a head coil 38 for scanning a subject positioned on the support structure (scanner bed) 39.

First lens assembly 42 and second lens assembly 44 are mounted to respective distal ends of first optical fibers 16 and second optical fibers 20 and positioned in the scanner borehole 36 for projecting and detecting pattern sequences on/from a surface region within the head coil 38.

As an alternative to the MR scanner shown in FIG. 1a, PET scanner comprising at least one detector ring in a scanner housing forming a scanner borehole could also be imagined. In this case, the distal ends of the respective optical fibers 16, 20 could be positioned outside the detector ring and near the scanner borehole for projecting and detecting pattern sequences on/from a surface region within the scanner borehole. Yet an alternative to the MR scanner of FIG. 1a is a combined MR/PET scanner.

FIG. 1a shows a surface scanning apparatus 2 which is positioned inside the scanner room defined by surrounding walls 52 illustrated by one wall/Faraday cage to the left side of the apparatus 2. A power management and/or controller part 50, e.g. a computer as illustrated in FIG. 1a, is positioned outside the scanner room. The surface scanning apparatus 2 may be positioned outside the scanner room defined by surrounding walls 52 if the optical fibers 16, 20 are sufficiently long.

In FIG. 1a is also shown an optical extender 54 which transfers image data noiseless between the surface scanning apparatus 2 and the computer 50 outside the scanner room. The apparatus 2 can be surrounded by a housing 4 which functions as a radio frequency shielded box. The housing 4 can be made out of a frame, e.g. a wooden frame, covered by a 1 mm copper layer. A filter of capacitors (not shown in the figure) ensures that the electromagnetic noise from powering the components inside the housing does not propagate along the power cable. The power supply optionally being a separate power supply or a part of the power management/controller part 50 is positioned outside the scanner room and the power is led through a filter in the wall 52 into the scanner room and the elements inside the housing 4 of the apparatus 2.

The distal ends of fibers are provided with respective first and second lens assemblies 42, 44 constituting projection optics and image capturing optics, respectively. A frame 46 is used for fixing the position between the first and second lens assemblies 42, 44 and/or between the distal ends of the first and second optical fibers 16, 18, respectively.

The first and second lens assemblies may each comprise an objective lens with a given focal length and aperture. Also, the second lens assembly may comprise a near infra-red (NIR) filter. Both first and second lens assemblies may comprise a first mirror/prism and/or second mirror/prism, respectively. The mirror/prism may be shared between the two lens assemblies.

Figure 1B:
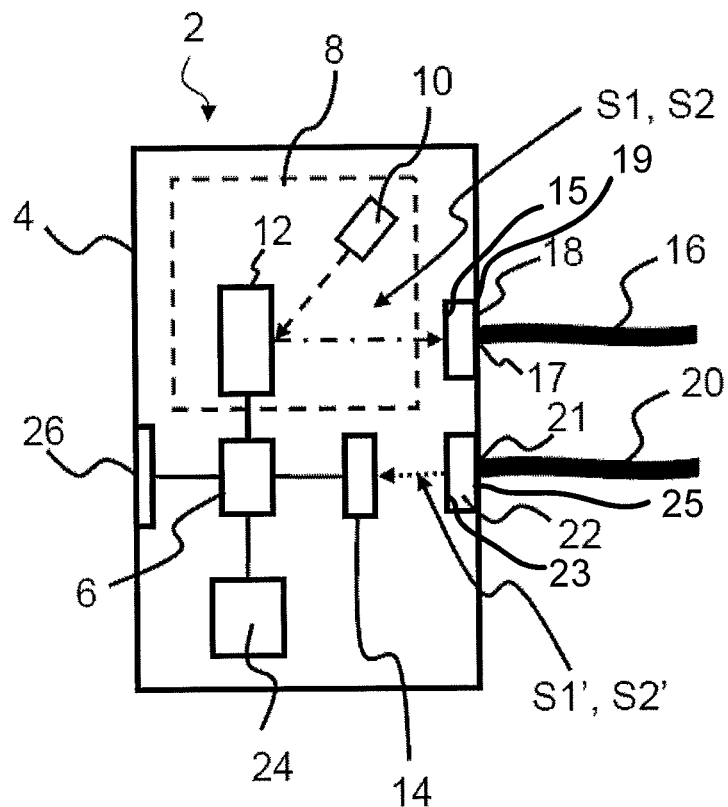

FIG. 1b schematically shows a surface scanning apparatus 2 of the present invention. The apparatus 2 comprises a housing 4 accommodating a control unit 6 and an image source 8 comprising a light source 10 and a light modulator 12. Further, the apparatus 2 optionally comprises a first camera 14 connected to the control unit 6 for exchange of control signals and/or pattern sequence data between the control unit 6 and the first camera 14. During use, first optical fibers 16 are coupled to the apparatus at the proximal ends 17 of the first optical fibers via first optical coupler 18 such that light from the image source 8 is coupled into the first optical fibers 16. The first optical coupler 18 has a proximal end 15 and a distal end 19.

The apparatus optionally comprises a memory unit 24 and a user interface unit 26.

The first optical fibers 16 may be fixedly mounted to the housing 4, i.e. the first optical fibers 16 may form a part of the apparatus 2. Alternatively, a distal end 19 of the first optical coupler 18 may be secured releasably to the proximal ends 17 of the first fiber bundle 16 by a click-release-coupling.

During use, second optical fibers 20 are coupled to the apparatus 2 at the proximal ends 21 of the second optical fibers 20 via second optical coupler 22 such that pattern sequences or images projected on the surface region is detected by the first camera 14. The second optical coupler 18 comprises a proximal end 23 and a distal end 25.

The first and second optical fibers may be fixedly mounted to the housing 4, i.e. the first and second optical fibers may form a part of the apparatus 2, thereby simplifying setting up the apparatus.

Alternatively, the distal end 19 of the first optical coupler 18 and/or the distal end 25 of the second optical coupler 22 may be secured releasably to the proximal ends 17 of the first fiber bundle 16 and the proximal ends 21 of the second fiber bundle 20, respectively, by a click-release-coupling.

The apparatus 2 is configured for projecting a first pattern sequence (S1) onto a surface region of the subject with the image source 10, wherein the subject is positioned in a scanner borehole of a medical scanner, the first pattern sequence optionally comprising a first primary pattern ($P_{1,1}$) and a first secondary pattern ($P_{1,2}$). The apparatus 2 may be configured for detecting the projected first pattern sequence (S1') with the first camera 14. The control unit 6 optionally determines a second pattern sequence (S2) comprising a second primary pattern ($P_{2,1}$) based on the detected first pattern sequence (S1') and sends control signals to the image source 8 with image source 10 and light modulator 12 projecting images in the form of the second pattern sequence (S2) onto a surface of the subject via the first optical coupler 18. The projected second pattern sequence (S2') may be detected with the first camera 14 and the pattern sequence data are processed in the control unit and/or in the first camera 14 and/or in external computer 50. Upon or during detection of pattern sequence data, the apparatus 2 or external computer 50 determines motion tracking parameters based on the detected second pattern sequence (S2').

Figure 2:
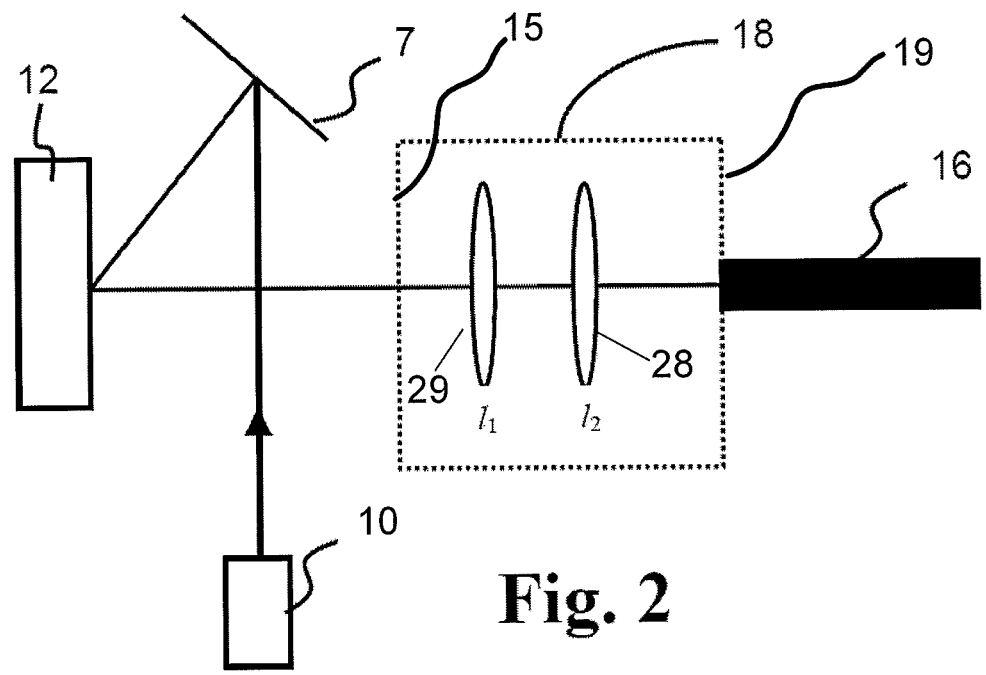
Figure 3:
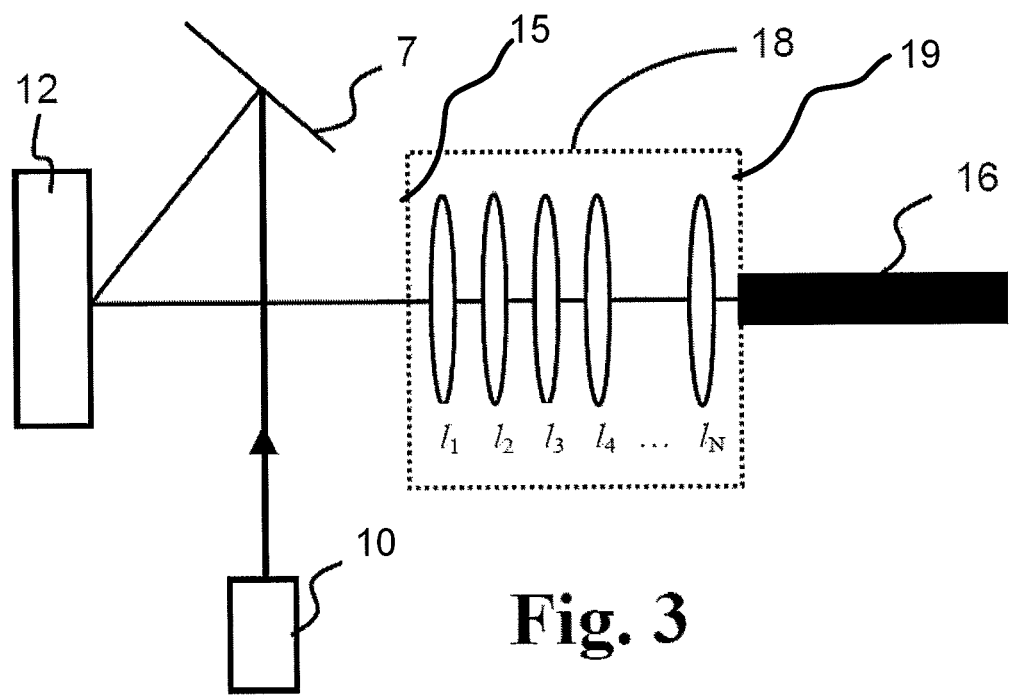
Figure 4:
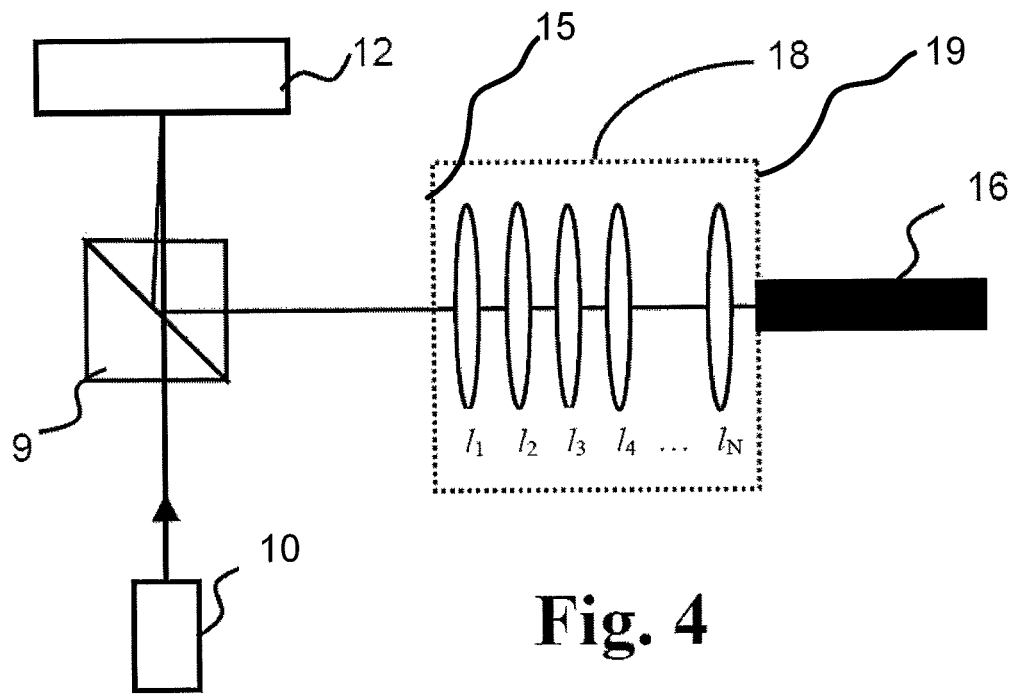
Figure 5:
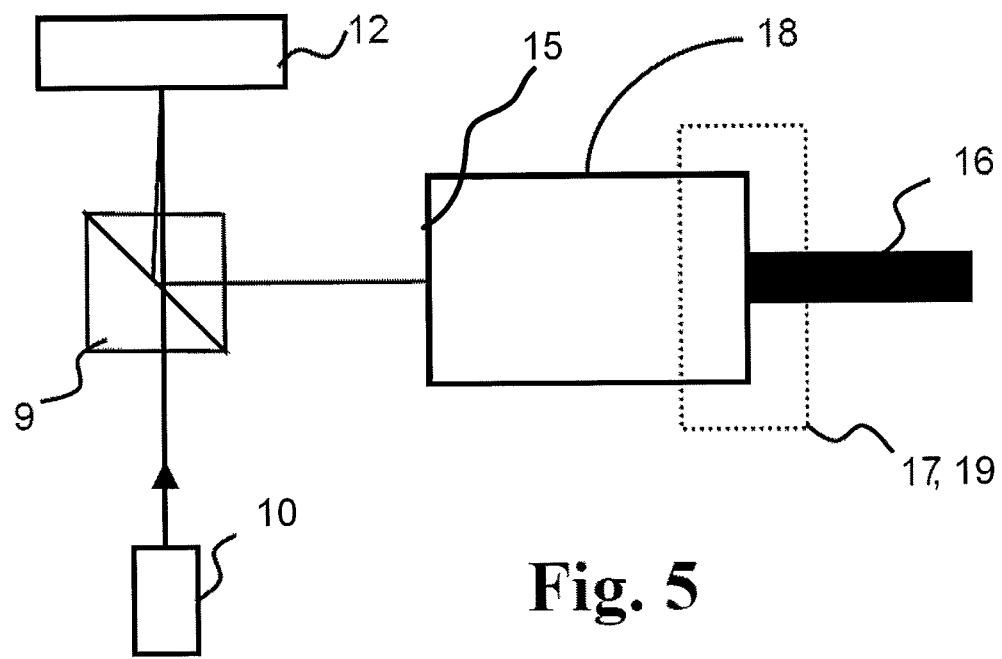

FIGS. 2-5 show different embodiments of the first optical coupler 18 comprising a plurality of lens elements $l_1, \ldots, l_N$, including a first lens element $l_1$ and a second lens element $l_2$. In FIG. 2, two lens elements are provided whereas FIGS. 3 and 4 show a large plurality of lens elements. In FIG. 5, the first optical coupler 18 is a relay lens coupler comprising or consisting of a number of N lens elements positioned inside an outer housing of the relay lens coupler. N may be six, eight or ten.

FIGS. 2-5 show only the first optical coupler 18, however the second optical coupler 22 may have an identical or different construction as the embodiments shown in FIGS. 2-5 for the first optical coupler 18. The following description of the lens elements in the first optical coupler 18 may therefore also apply to the lens elements in the second optical coupler 22.

Each lens element of the plurality of lens elements $l_1, \ldots, l_N$ comprises a primary surface 28 facing a distal end 19 of the first optical coupler 18, and a secondary surface 29 facing a proximal end 15 of the first optical coupler 18. Normally, there will be an even number of lens elements in the first and/or second optical coupler 18, 22. There may be two, four, six, eight, ten, twelve or more lens elements $l_1, \ldots, l_N$.

One or more of the lens elements $l_N$ may be achromatic, e.g. at least one of the plurality of lens elements is achromatic. In FIG. 2-5 only chromatic lens elements are shown.

In one or more embodiments, the first lens element $l_1$ is positioned at the proximal end 15 of the first optical coupler 18 and the second lens $l_2$ element is positioned at the distal end 19 of the first optical coupler 18, as shown in FIG. 2. In FIG. 2, both lens elements are chromatic. However, the first lens element $l_1$ and the second element $l_2$ could also be achromatic with convex sides pointing towards each other.

In the apparatus, mirrors and/or prisms may be used to guide the image from the image source 8 to the first optical coupler 18. In FIGS. 2 and 3, a mirror 7 is used for guiding the image from the image source to the light modulator 12 from where it is guided to the proximal end 15 of the first optical coupler 18. In FIGS. 4 and 5, the image passes from the image source 8 through a prism 9 to the light modulator 12 from where it again passes through the prism 9 in such a manner that the image is guided directly into the proximal end 15 of the first optical coupler 18.

The first and/or second optical coupler 18, 22 may be adapted for either increasing or decreasing the size of the image and/or the projected image, respectively such that the size of the image/projected image is either larger or smaller after having passed through the first and/or second optical coupler.

Figure 6A:
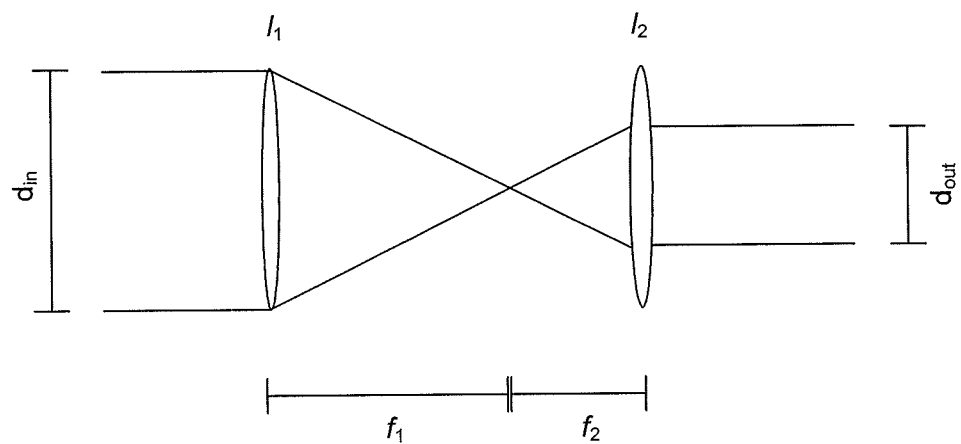
Figure 6B:
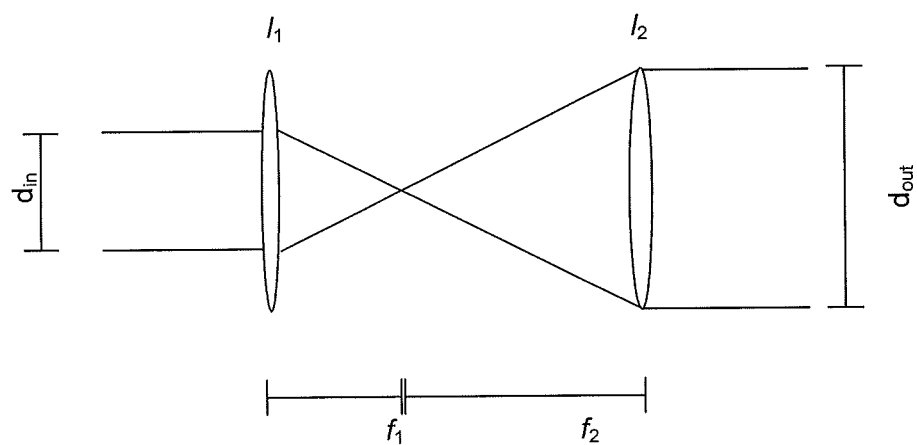

A simple schematic illustration of how the image size can be increased or decreased using an optical coupler is shown in FIG. 6a-b. In FIG. 6a, the image size is decreased from a size $d_{in}$ of the incoming image to a size of $d_{out}$ of the outcoming image, where $d_{in} > d_{out}$, whereas in FIG. 6b, the image size is increased from $d_{in}$ of the incoming image to a size of $d_{out}$, where $d_{in} > d_{out}$. The different focal length $f_1$, $f_2$ of the lens elements are illustrated in the figures.

By utilizing more than two lens elements, an improved correction and reduced (geometric) distortion may be obtained. Further, aberration effects are reduced. This allows the user to control the how large a part of the image which is coupled into the first optical fibers 16 and control the size of the projected image, which comes out of the second optical coupler 22 after having been collected by the second optical fibers 20.

Figure 7A:
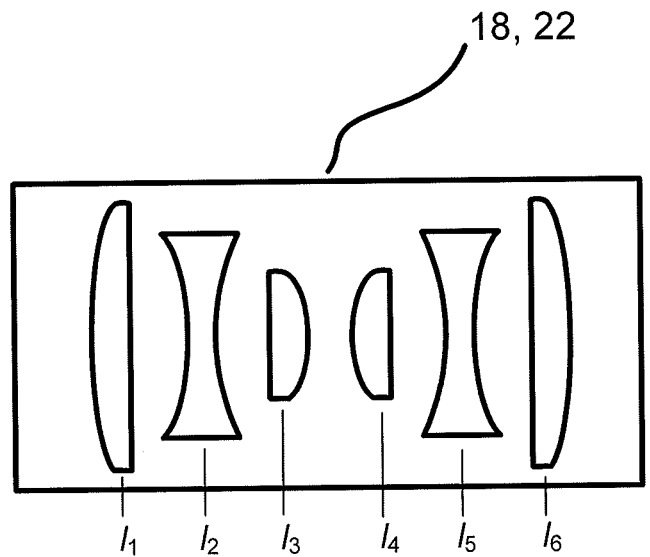
Figure 7B:
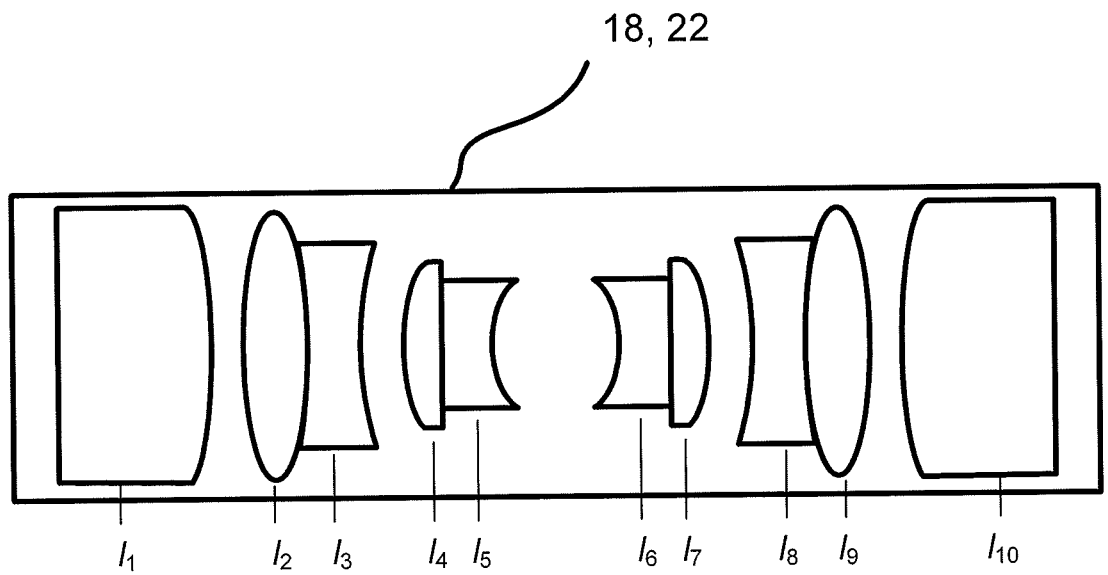

FIGS. 7a-b show two different examples of a relay lens couplers which may be used in the invention as the first optical coupler 18 and/or the second optical coupler 22.

In FIG. 7a, the relay coupler comprises or consist of six lens elements $l_1, l_2, l_3, l_4, l_5, l_6$ arranged symmetrically such that the outermost lens elements $l_1, l_6$ are nearly identical in size oriented such that they are a mirror image each other. Likewise, the lens elements $l_2, l_5$ positioned adjacent to the outermost lens elements $l_1, l_6$ form a mirror image pair and so forth for the next lens elements approaching the middle of the relay lens coupler. Four of the lens elements $l_1, l_3, l_4, l_6$ are planoconvex, i.e. they have a convex side and a plane side, whereas the other two lens elements $l_2, l_5$ are biconcave, i.e. both the primary and the secondary side of the lens elements are concave.

FIG. 7b shows a relay lens coupler comprising ten lens elements $l_1, l_2, l_3, l_4, l_5, l_6, l_7, l_8, l_9, l_{10}$ again arranged symmetrically with the lens elements pair wise from the two outermost lens elements towards the centre of the relay lens coupler being mirror images of one another. In FIG. 7a, four of the lens elements $l_1, l_4, l_7, l_{10}$ are planoconvex, two of the lens elements $l_3, l_8$ are biconcave, two of the lens elements $l_2, l_9$ are biconvex, i.e. both the primary and the secondary side of the lens elements are convex, and the last two elements $l_5, l_6$ are planoconcave, i.e. they have a concave side and a plane side.

The number of lens elements pairs is not limited to the examples shown in FIG. 7a-b. Further the combination of sizes and shapes of the lens elements may also vary, e.g. different combinations of planoconcave, planoconvex, biconcave, and/or biconvex lens element pairs positioned such they form a mirror image of one another could also be imagined.

It should be noted that in addition to the exemplary embodiments of the invention shown in the accompanying drawings, the invention may be embodied in different forms and should not be construed as limited to the embodiments set forth herein. Rather, these embodiments are provided so that this disclosure will be thorough and complete, and will fully convey the concept of the invention to those skilled in the art.

REFERENCES

2 Apparatus
4 Housing
6 Control unit
7 Mirror
8 Image source
9 Prism
10 Light source
12 Light modulator
14 First camera
15 Proximal end of the first optical coupler
16 First optical fibers
17 Proximal ends of first optical fibers
18 First optical coupler
19 Distal end of the first optical coupler
20 Second optical fibers
21 Proximal ends of second optical fibers
22 Second optical coupler
23 Proximal end of the second optical coupler
24 Memory
25 Distal end of the second optical coupler
26 User interface
28 Primary surface of the lens elements
29 Secondary surface of the lens elements
30 Medical scanner
32 Magnet
34 Scanner housing
36 Scanner borehole
38 Head coil
39 Scanner bed
40 Subject
42 First lens assembly
44 Second lens assembly
46 Frame
50 Power management part
52 Wall surrounding the scanner room
54 Optical extender
$l_N$ N'th lens element
$l_1$ First lens element
$l_2$ Second lens element
$l_3$ Third lens element
$l_4$ Fourth lens element
$l_5$ Fifth lens element
$l_6$ Sixth lens element
$l_7$ Seventh lens element
$l_8$ Eights lens element
$l_9$ Ninths lens element
$l_{10}$ Tenths lens element
$d_{in}$ Size of the image before entering the first/second optical coupler
$d_{out}$ Size of the image after exiting the first/second optical coupler
$f_1$ Focal length of the first lens element
$f_2$ Focal length of the second lens element

The invention claimed is:

1. A method for surface scanning of a surface region of a subject in medical imaging, the method comprising:
providing an image source, wherein the image source comprises a digital micromirror device (DMD) chip or light modulator and the image source has a resolution of 480×320 pixels or more;
providing a first optical coupler having a proximal end and a distal end and comprising a plurality of lens elements including a first lens element and a second lens element;
providing a first fiber bundle comprising first optical fibers having proximal ends and distal ends, wherein the number of first optical fibers is larger than 1,000, and the first fiber bundle has a length larger than 1 meter;
positioning the distal ends of the first optical fibers within a scanner borehole of a medical scanner;
feeding an image from the image source into the proximal end of the first optical coupler and forming a passed image at the distal end of the first optical coupler;
feeding the passed image from the distal end of the first optical coupler into the proximal ends of the first optical fibers;
providing a second optical coupler comprising a plurality of lens elements including a first lens element and a second lens element;

providing a second fiber bundle comprising second optical fibers having proximal ends and distal ends;
positioning the distal ends of the second optical fibers within the scanner borehole of the medical scanner;
capturing a projected image from the subject in the borehole by the distal ends of the second optical fibers; and
feeding the projected image from the proximal end of the second optical fibers into the second optical coupler.

2. Method according to claim 1, wherein the image source includes a digital micromirror device (DMD) chip.

3. Method according to claim 1, wherein the image source comprises a light source, and a mirror or a prism is used to guide light from the light source towards the first optical coupler.

4. Method according to claim 1, wherein the first optical coupler is a relay lens coupler.

5. Method according to claim 1, wherein the distal end of the first optical coupler is releasably secured to the proximal end of the first fiber bundle by a click-release-coupling.

6. Method according to claim 1, wherein the distal end of the first optical coupler is fixed non-releasably to the proximal end of the first fiber bundle.

7. Method according to claim 1, wherein feeding an image from the image source comprises feeding a pattern sequence comprising a plurality of different patterns.

8. Method according to claim 1, further comprising:
arranging a first lens assembly at the distal ends of the first optical fibers, and
coupling images from the first optical fibers to the surface region of the subject via the first lens assembly.

9. Method according to claim 1, further comprising:
arranging a second lens assembly at the distal ends of the second optical fibers, and
coupling images from surface region of the subject to the second optical fibers via the second lens assembly.

10. Method according to claim 1, wherein the image source is connected to a control unit, said image source receiving control signal(s) comprising a pattern sequence selector, wherein the image source is configured for projecting different pattern sequences dependent on the pattern sequence selector.

11. Method according to claim 10, wherein a number of different pattern sequences are stored in the image source, and the image source is configured to project a selected pattern sequence based on the pattern sequence selector from the control unit.

12. Surface scanning apparatus for surface scanning of a surface region of a subject in medical imaging, the apparatus comprising:
an image source having a resolution of 480×320 pixels or more, wherein the image source comprises a digital micromirror device (DMD) chip or light modulator,
a first optical fiber bundle comprising first optical fibers having proximal ends and distal ends, wherein the number of first optical fibers is larger than 1,000 and the first fiber bundle has a length larger than 1 meter,
a first optical coupler for coupling an image from the image source into the proximal ends of the first optical fibers,
wherein the first optical coupler has a proximal end for receiving an image from the image source and a distal end for feeding a passed image into the proximal ends of the first optical fibers,
wherein the first optical coupler comprises a plurality of lens elements including a first lens element and a second lens element, each of the plurality of lens elements comprising a primary surface facing the distal end of the first optical coupler, and a secondary surface facing the proximal end of the first optical coupler;
a second optical coupler comprising a plurality of lens elements including a first lens element and a second lens element; and
a second fiber bundle comprising second optical fibers having proximal ends and distal ends; wherein the distal ends of the second optical fibers are within the scanner borehole of the medical scanner;
wherein the surface scanning apparatus is adapted to capture a projected image from the subject in the borehole by the distal ends of the second optical fibers, and feed the projected image from the proximal end of the second optical fibers into the second optical coupler.

13. Surface scanning apparatus according to claim 12, wherein the image source includes a digital micromirror device (DMD) chip.

14. Surface scanning apparatus according to claim 12, wherein the first optical coupler comprises an even number of lens elements.

15. Surface scanning apparatus according to claim 12, wherein the first optical coupler is a relay lens coupler.

16. Surface scanning apparatus according to claim 12, wherein the distal end of the first optical coupler is releasably secured to the proximal end of the first fiber bundle by a click-release-coupling.

17. Surface scanning apparatus according to claim 12, wherein at least one of the plurality of lens elements is achromatic.

18. Surface scanning apparatus according to claim 12 wherein the first lens element is positioned at the proximal end of the first optical coupler and the second lens element is positioned at the distal end of the first optical coupler, wherein the first lens element and the second element are achromatic with convex sides pointing towards each other.

19. Surface scanning apparatus according claim 12, wherein the primary surface of each of the plurality of lens elements is concave or convex, and the secondary surface of each of the plurality of lens elements is concave or convex.

20. Surface scanning apparatus according claim 12, further comprising a first lens assembly arranged at and/or attached to the distal ends of the first optical fibers for coupling images from the first optical fibers to the surface region of the subject.

21. Surface scanning apparatus according to claim 12, further comprising:
a second lens assembly arranged at and/or attached to the distal ends of the second optical fibers for coupling images from the surface region of the subject to the second optical fibers.

22. Surface scanning apparatus according to claim 12, wherein the image source is connected to a control unit, said image source adapted to receive control signal(s) comprising a pattern sequence selector, wherein the image source is configured for projecting different pattern sequences dependent on the pattern sequence selector.

23. Surface scanning apparatus according to claim 22, wherein a number of different pattern sequences are stored in the image source, and the image source is configured to project a selected pattern sequence based on the pattern sequence selector from the control unit.

* * * * *